United States Patent
Fan

(10) Patent No.: US 8,319,629 B2
(45) Date of Patent: Nov. 27, 2012

(54) ALARM SYSTEM AND METHOD

(75) Inventor: Chao-Tsung Fan, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 580 days.

(21) Appl. No.: 12/606,197

(22) Filed: Oct. 27, 2009

(65) Prior Publication Data

US 2011/0037587 A1    Feb. 17, 2011

(30) Foreign Application Priority Data

Aug. 13, 2009   (CN) .......................... 2009 1 0305580

(51) Int. Cl.
*G08B 1/08* (2006.01)
(52) U.S. Cl. ................. 340/539.1; 340/568.1; 340/10.1
(58) Field of Classification Search ............... 340/539.1, 340/572.1, 568.1, 572.2–572.9, 540, 10.1, 340/10.3, 10.51, 10.52, 10.5, 573.1
See application file for complete search history.

(56) References Cited

U.S. PATENT DOCUMENTS

| | | | | |
|---|---|---|---|---|
| 6,002,344 A * | 12/1999 | Bandy et al. | ................. | 340/10.2 |
| 7,468,650 B2 * | 12/2008 | Childress et al. | ............ | 340/5.92 |
| 7,898,414 B2 * | 3/2011 | Spano | ........................... | 340/571 |
| 2006/0077040 A1 * | 4/2006 | Bormaster | .................... | 340/10.2 |
| 2007/0206797 A1 * | 9/2007 | Chan et al. | .................... | 380/270 |
| 2008/0272888 A1 * | 11/2008 | Cardwell et al. | ............. | 340/10.1 |

FOREIGN PATENT DOCUMENTS

CN   101436317 A   5/2009

* cited by examiner

*Primary Examiner* — Daniel Previl
(74) *Attorney, Agent, or Firm* — Altis Law Group, Inc.

(57) ABSTRACT

An alarm system includes a number of radio frequency identification (RFID) tags, an RFID reader, a warning unit, and a control module. The RFID reader receives radio-frequency signals from some of the number of the RFID tags via an antenna when the some of the number of the RFID tags are in a determined area around the RFID reader. The control module activates the warning unit when a radio-frequency signal from at least one of the number of RFID tags is not received by the RFID reader.

10 Claims, 3 Drawing Sheets

ALARM SYSTEM AND METHOD

BACKGROUND

1. Technical Field

The present disclosure relates to an alarm system and a method for the alarm system.

2. Description of Related Art

In care-giving institutions, staff are often required to locate some or all patients quickly. Such a requirement is even more important when clients are involved in outdoor activities or during transport.

DETAILED DESCRIPTION

Figure 1:
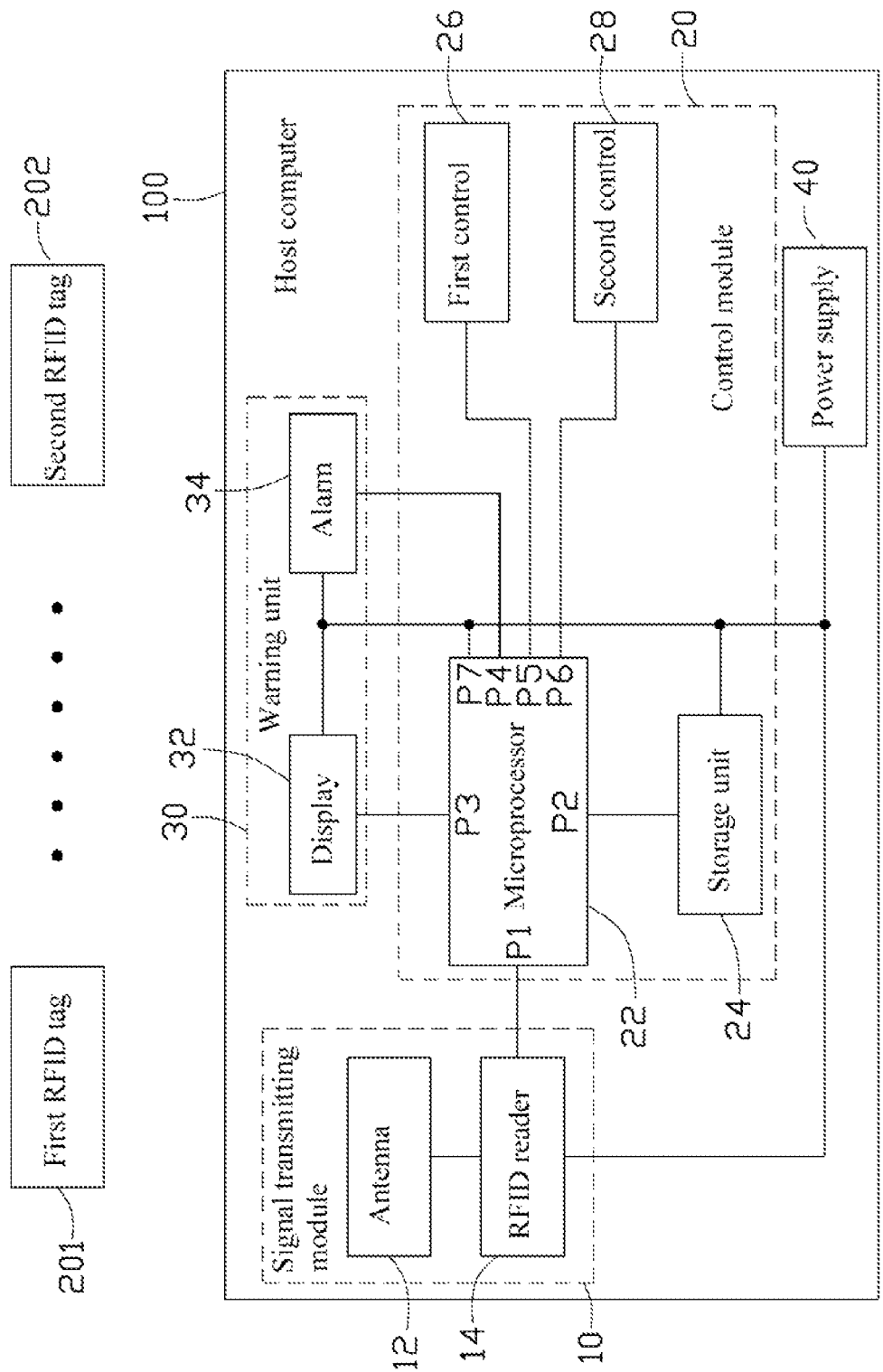
FIG. 1 is a schematic diagram of an exemplary embodiment of an alarm system, the alarm system includes a microprocessor.

Referring to FIG. 1, an exemplary embodiment of an alarm system 1 includes a host computer 100 and a plurality of radio frequency identification (RFID) tags. The alarm system 1 issues notification when clients or residents with a RFIF tag are beyond a determined area. The host computer 100 is located at the determined area or on staff's person. Each RFID tag is encoded with representing a client or resident.

The host computer 100 includes a signal transmitting module 10, a control module 20, a warning unit 30, and a power supply 40.

The signal transmitting module 10 includes an antenna 12 and an RFID reader 14. The RFID reader 14 is connected to the antenna 12 and receives radio-frequency signals from the RFID tags. The radio-frequency signals include identification of the codes of the corresponding RFID tags. It can be understood that when the RFID tag is in the determined area, the radio-frequency signal from the RFID tag can be received by the RFID reader 14. The RFID reader 14 may be at a center of the determined area. A maximum distance that the RFID reader 14 can receive the radio-frequency signals from the RFID tags may be a radius of the determined area.

The warning unit 30 includes a display 32 and an alarm 34.

The control module 20 includes a microprocessor 22, a storage unit 24, a first control 26, and a second control 28. An input terminal P1 of the microprocessor 22 is connected to the RFID reader 14. A storage terminal P2 of the microprocessor 22 is connected to the storage unit 24. A first output terminal P3 is connected to the display 32. A second output terminal P4 is connected to the alarm 34. A first control terminal P5 of the microprocessor 22 is connected to the first control 26. A second control terminal P6 of the microprocessor 22 is connected to the second control 28. The microprocessor 22 reads radio-frequency signals from the RFID reader 14.

When the first control terminal P5 is at a high level, such as 5V, the microprocessor 22 reads the radio-frequency signals from the RFID reader 14, and stores the corresponding codes according to the detected RFID tags. It can be understood that when the first control 26 is activated, the first control terminal P5 is at a high level.

When the first control terminal P5 is at a low level, such as 0V, the microprocessor 22 compares the codes of the radio-frequency signals read from the RFID reader 14 with the codes stored in the storage unit 24 to determine whether radio-frequency signals from all RFID tags have been received by the RFID reader 14. It can be understood that when the first control 26 is released, namely un-pressed, the first control terminal P5 is at a low level.

Figure 2:
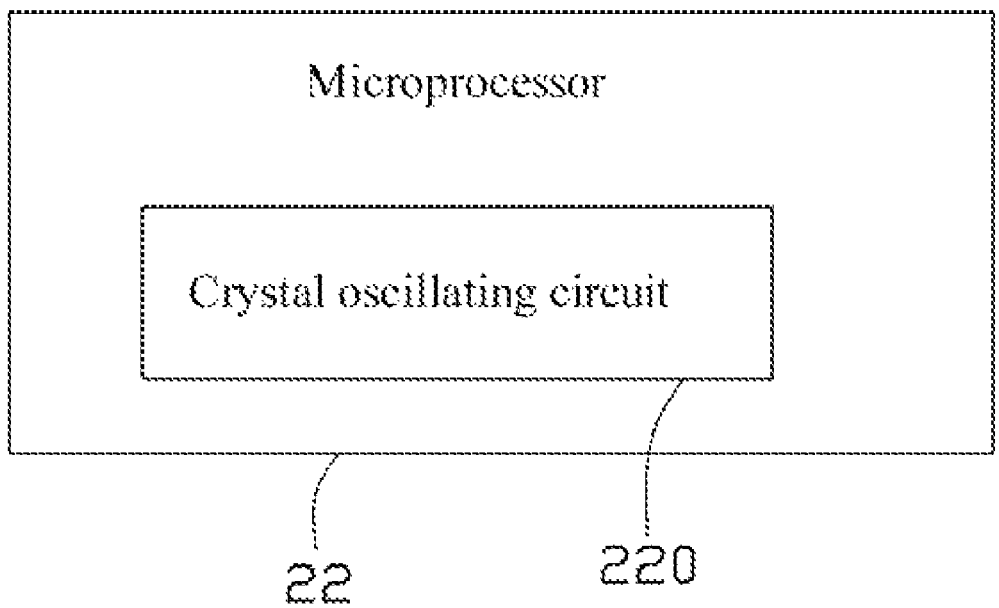
FIG. 2 is a schematic diagram of the microprocessor in FIG. 1.

Referring to FIG. 2, the microprocessor 22 also includes a crystal oscillating circuit 220 providing clock frequency. It can be understood that the clock frequency is related to the cycle in which the microprocessor 22 reads the radio-frequency signals from the RFID reader 14. In the embodiment, the clock frequency can be adjusted via the second control 28. For example, an initial cycle in which the microprocessor 22 reads the radio-frequency signals from the RFID reader 14 is two seconds. When the second control 28 is activated a first time, the cycle in which the microprocessor 22 reads the radio-frequency signals from the RFID reader 14 is four seconds. When the second control 28 is activated a second time, the cycle in which the microprocessor 22 reads the radio-frequency signals from the RFID reader 14 is six seconds.

The power supply 40 is connected to a power terminal P7 of the microprocessor 22, the RFID reader 14, the storage unit 24, the display 32, and the alarm 34, providing power thereto.

In use, each RFID tag is attached to an individual client or resident. In the embodiment, the alarm system 1 as disclosed includes a first RFID tag 201 and a second RFID 202. The first RFID tag 201 is worn by Client A. The second RFID tag 202 is worn by Client B. The first RFID tag 201 is encoded with "001." The second RFID tag 202 is encoded with "002." The first RFID tag 201 emits a first radio-frequency signal which includes identification of the code "001." The second RFID tag 202 emits a second radio-frequency signal which includes identification of the code "002."

The RFID reader 14 receives the first and second radio-frequency signals emitted from the first RFID tag 201 and the second RFID tag 202 via the antenna 12, and transmits the first and second radio-frequency signals to the microprocessor 22.

When the first control 26 is activated, the microprocessor 22 reads the information of the first and second radio-frequency signals, to obtain the codes "001" and "002", and stores the codes and names of Client A and Client B linked with the corresponding tag's code in the storage unit 24.

When the first control 26 is released, the microprocessor 22 reads the information of the radio-frequency from the RFID reader 14 with a preset cycle, such as ten seconds. If Client A is no longer within the determined area, the RFID reader 14 receives the second radio-frequency signal from the RFID tag 202 but not the first radio-frequency signal from the RFID tag 201. The microprocessor 22 compares the code "002" with data stored in the storage unit 24, and determines that the code "001" has not been read. As a result, the microprocessor 22 outputs a first control signal to the display 32 and the alarm 34. The first control signal includes the code "001" and the name Client A. The display 32 displays the name Client A. The alarm 34 issues notification that Client A is no longer within the determined area.

Figure 3:
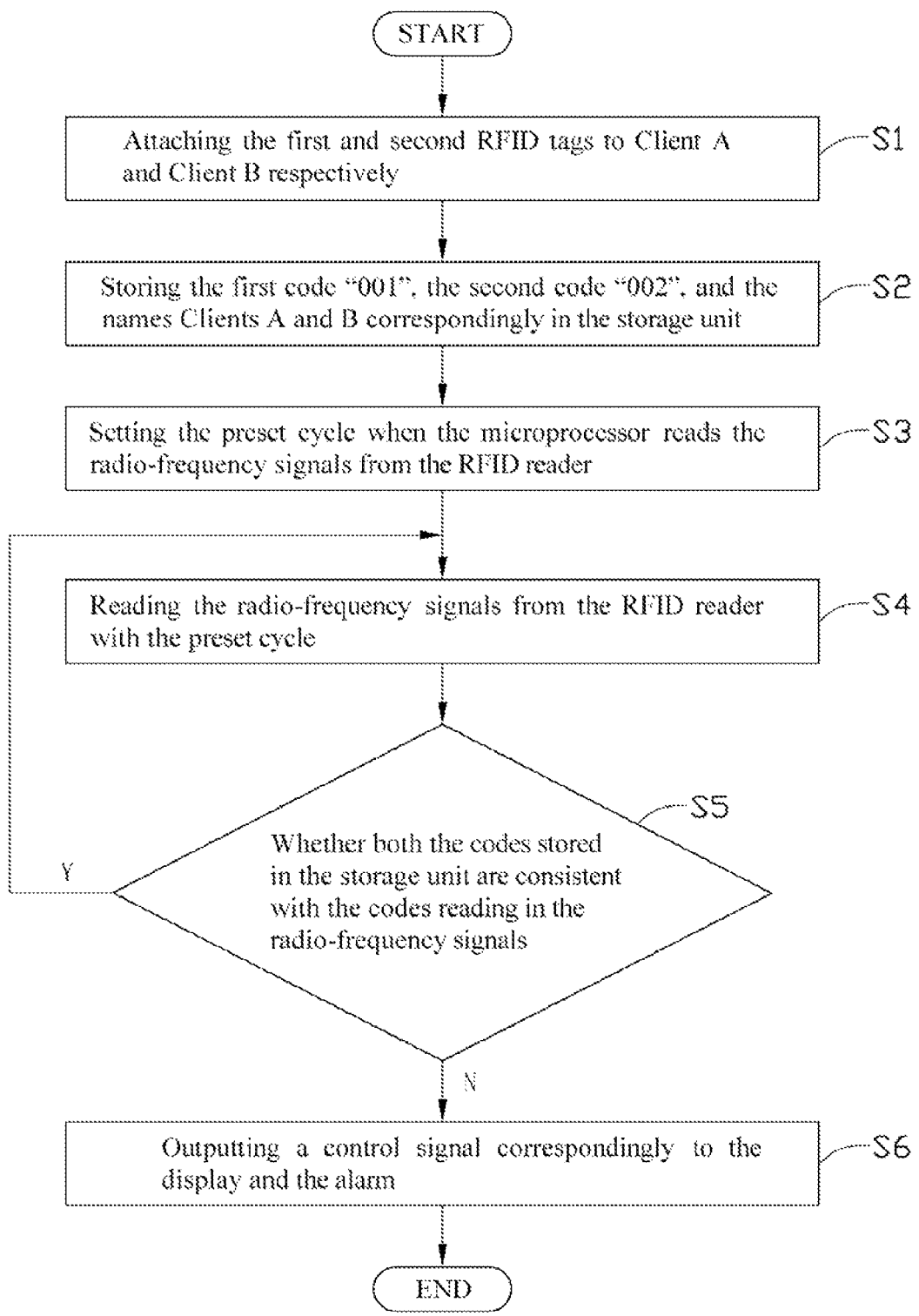
FIG. 3 is a flowchart of an exemplary embodiment of an alarm method.

Referring to FIG. 3, an exemplary embodiment of an alarm method includes the following.

In step S1, a first RFID tag 201 and a second RFID tag 202 are attached to Client A and Client B respectively.

In step S2, Client A and Client B are in the determined area. The RFID reader 14 receives first and second radio-frequency signals respectively from first RFID tag 201 and second RFID tag 202. The microprocessor 22 reads the radio-frequency signals from the RFID reader 14. The first control 26 is activated, directing microprocessor 22 to store the first code "001," the second code "002," and the names Client A and Client B linked with the corresponding tag's code in the storage unit 24.

In step S3, the preset cycle in which the microprocessor 22 reads the first and second radio-frequency signals from the RFID reader 14, such as ten seconds, is set via the second control 28.

In step S4, the microprocessor 22 reads radio-frequency signals from the RFID reader 14 with the preset cycle.

In step S5, the microprocessor 22 compares the codes read in the radio-frequency signals with the codes stored in the storage unit 24, and determines whether both codes stored in the storage unit 24 are consistent with those read in the radio-frequency signals. When all the codes stored in the storage unit 24 are consistent with the codes read in the radio-frequency signals, step S4 is repeated. When not all codes stored in the storage unit 24 are consistent with those read in the radio-frequency signals, step S6 is implemented. For example, if Client A is no longer within the determined area, the RFID reader 14 receives only the second radio-frequency signal from the RFID tag 202 but not the second radio-frequency signal from the RFID tag 201. The microprocessor 22 compares the code "002" with the codes stored in the storage unit 24, and determines that the code "001" has not been read.

In step S6, the microprocessor 22 outputs a control signal correspondingly to the display 32 and the alarm 34. The display 32 displays the name corresponding to the code which has not been read by the microprocessor 22. The alarm 34 issues a notification that at least one client is no longer within the determined area. In an example, the display 32 shows the name Client A to notify staff of the missing client.

The foregoing description of the exemplary embodiments of the disclosure has been presented only for the purposes of illustration and description and is not intended to be exhaustive or to limit the disclosure to the precise forms disclosed. Many modifications and variations are possible in light of the above everything. The embodiments were chosen and described in order to explain the principles of the disclosure and their practical application so as to enable others of ordinary skill in the art to utilize the disclosure and various embodiments and with various modifications as are suited to the particular use contemplated. Alternative embodiments will become apparent to those of ordinary skills in the art to which the present disclosure pertains without departing from its spirit and scope. Accordingly, the scope of the present disclosure is defined by the appended claims rather than the foregoing description and the exemplary embodiments described therein.

What is claimed is:

1. An alarm system comprising:
a plurality of radio frequency identification (RFID) tags;
an RFID reader to receive radio-frequency signals from the plurality of RFID tags via an antenna, when the plurality of RFID tags are in a determined area surrounding the RFID reader;
a warning unit; and
a control module to activate the warning unit when the radio-frequency signal from at least one of the plurality of RFID tags is not received by the RFID reader, wherein each RFID tag is encoded and the control module comprises a microprocessor and a storage unit; wherein the storage unit stores all the codes of the plurality of RFID tags, the microprocessor reads radio-frequency signals from the RFID reader and compares the codes of the radio-frequency signals read by the microprocessor with the codes stored in the storage unit.

2. The alarm system of claim 1, wherein the warning unit comprises an alarm.

3. The alarm system of claim 1, wherein the microprocessor comprises a control terminal, according to which, when at a high level, the microprocessor stores the codes of the plurality of RFID tags in the storage unit, and when at a low level, the microprocessor compares codes from the radio-frequency signals read by microprocessor with the codes stored in the storage unit.

4. The alarm system of claim 3, wherein the control module further comprises a control, according to which, when activated, the control terminal of the microprocessor is at a high level, and, when released, the control terminal of the microprocessor is at a low level.

5. The alarm system of claim 1, wherein the microprocessor further comprises a crystal oscillating circuit and a control terminal, the crystal oscillating circuit providing a cycle in which the microprocessor reads radio-frequency signals from the RFID reader, and the control terminal adjusts the cycle of the crystal oscillating circuit.

6. The alarm system of claim 5, wherein the control module further comprises a control, connected to the control terminal and adjusting the cycle of the crystal oscillating circuit.

7. The alarm system of claim 1, wherein each RFID tag represents an individual, the identification of the individual is stored in the storage unit and linked with the tag's code.

8. The alarm system of claim 7, wherein the warning unit further comprises a display providing identification of the individual represented by the tag, the radio-frequency of which has not been received by the RFID reader.

9. An alarm method comprising:
storing codes corresponding to a plurality of radio frequency identification (RFID) tags in a storage unit;
an RFID reader receiving radio-frequency signals from those of the plurality of RFID tags within a determined area;
a microprocessor reading the radio-frequency signals from the RFID reader;
the RFID reader determining whether radio-frequency signals from all of the plurality of RFID tags have been received, wherein determination of whether the radio-frequency signals from all of the plurality of RFID tags are received by the RFID reader comprises:
comparing the codes of the radio-frequency signals read by the microprocessor with the codes stored in the storage unit;
when the codes of the radio-frequency signals read by the microprocessor are the same as the codes stored in the storage unit, the microprocessor determines that the radio-frequency signals from all of the plurality of RFID tags have been received by the RFID reader; and
when the codes of the radio-frequency signals read by the microprocessor are not the same as the codes stored in the storage unit, the microprocessor determines that not all the radio-frequency signals from the plurality of RFID tags have been received by the RFID reader; and
the RFID reader activating a warning unit when a radio-frequency signal from at least one of the plurality of RFID tags is not received.

10. The alarm method of claim 9, wherein each RFID tag represents an individual, the identification of the individual is stored in the storage unit and linked with each tag's code, and the warning unit comprises a display, and wherein activation of the warning unit comprises:
displaying the identification of each individual corresponding to an RFID tag the radio-frequency signal of which has not been received by the RFID reader.

* * * * *